United States Patent
Naeger

(10) Patent No.: US 11,986,479 B2
(45) Date of Patent: May 21, 2024

(54) COMBINATION DRUG PRODUCTS FOR TREATING PATIENTS SUFFERING FROM ONE OR MORE MEDICAL CONDITIONS CAUSED BY CORONAVIRUS INFECTION, INCLUDING BY SARS-CoV-2, ITS ALPHA, BETA, DELTA, OR OMICRON VARIANTS AND SUB VARIANTS

(71) Applicant: PharSoln, Inc., Arlington, VA (US)

(72) Inventor: David M. Naeger, Gainesville, VA (US)

(73) Assignee: PHARSOLN, INC., Arlington, VA (US)

( * ) Notice: Subject to any disclaimer, the term of this patent is extended or adjusted under 35 U.S.C. 154(b) by 0 days.

(21) Appl. No.: 18/110,238

(22) Filed: Feb. 15, 2023

(65) Prior Publication Data

US 2024/0024329 A1      Jan. 25, 2024

Related U.S. Application Data

(60) Provisional application No. 63/413,045, filed on Oct. 4, 2022, provisional application No. 63/391,414, filed on Jul. 22, 2022.

(51) Int. Cl.
| | | |
|---|---|---|
| *A61K 31/52* | (2006.01) | |
| *A61K 31/145* | (2006.01) | |
| *A61K 31/573* | (2006.01) | |
| *A61P 31/14* | (2006.01) | |

(52) U.S. Cl.
CPC ............ *A61K 31/52* (2013.01); *A61K 31/145* (2013.01); *A61K 31/573* (2013.01); *A61P 31/14* (2018.01)

(58) Field of Classification Search
CPC .... A61K 31/52; A61K 31/145; A61K 31/573; A61P 31/14
See application file for complete search history.

(56) References Cited

U.S. PATENT DOCUMENTS

| | | |
|---|---|---|
| 2022/0062232 A1 | 3/2022 | Owen et al. |
| 2022/0175869 A1 | 6/2022 | Zaid et al. |

FOREIGN PATENT DOCUMENTS

| | | |
|---|---|---|
| WO | 2022061171 A1 | 3/2022 |
| WO | 2022115952 A1 | 6/2022 |
| WO | 2022126207 A1 | 6/2022 |

OTHER PUBLICATIONS

Tamburin et al. Internal and Emergency Medicine, 2021, vol. 16, pp. 1729-1731 (Year: 2021).*
Fillmore et al. PLOS One, Oct. 28, 2021, vol. 16, No. 10, e0259061, 9 pages (Year: 2021).*
NCT04594343 (ClinicalTrials.gov, Last Update Posted Oct. 8, 2021, 10 pages) (Year: 2021).*
Lee et al. Gut, Apr. 2021, vol. 70, No. 4, pp. 632-634 (Year: 2021).*
Zhou et al. Cell Discovery, 2020, vol. 6, No. 14, 18 pages (Year: 2020).*
Vardhan et al. Coronaviruses, 2021, vol. 2, pp. 415-418 (Year: 2021).*
Purinethol Product Label (Stason Pharmaceuticals, Revised Dec. 2020, 9 pages) (Year: 2020).*
Marrone et al. CID, 2022, vol. 75, pp. e403-e409) (Published Online Jan. 27, 2022) (Year: 2022).*
Domling et al., "Chemistry and Biology of SARS-CoV-2", Chem 6, 1283-1295, Jun. 11, 2020.
Lin et al., "Disulfiram can inhibit MERS and SARS coronavirus papain-like proteases via different modes", Antiviral Research 150 (2018) 155-163.
Salasc, F. et al. "Treatments for COVID-19: Lessons from 2020 and New Therapeutic Options." Current Opinion in Pharmacology, vol. 62, Feb. 2022, pp. 43-59.

* cited by examiner

*Primary Examiner* — James D. Anderson
(74) *Attorney, Agent, or Firm* — Banner & Witcoff, Ltd.

(57) ABSTRACT

Treatments for human subjects exposed to, potentially exposed to, infected by, or potentially infected by a coronavirus, such as SARS-CoV-2, its variants and sub variants are described, which are based on an administration of combination drug products having two or three active ingredients formulated with one or more pharmaceutically acceptable carriers. These patients (children, adults and the elderly) suffer from symptoms of COVID-19, and some may continue to suffer from its aftereffects many weeks or months after an infection, like long COVID, including neurological symptoms such as brain fog and confusion. Physiological ailments may consist of symptoms such as fatigue, shortness of breath, difficulty breathing, joint and muscle aches, and the like. The two-component combination drug product comprises effective amounts of ANTABUSE (disulfiram) and PURINETHOL (mercaptopurine, 6-mercaptopurine, or 6-MP) or its prodrug IMURAN (azathioprine) or hydrates of these compounds. A three-component combination drug product adds, in addition to the foregoing active ingredients, an effective amount of dexamethasone or pharmacologically acceptable salts thereof.

9 Claims, No Drawings

COMBINATION DRUG PRODUCTS FOR TREATING PATIENTS SUFFERING FROM ONE OR MORE MEDICAL CONDITIONS CAUSED BY CORONAVIRUS INFECTION, INCLUDING BY SARS-CoV-2, ITS ALPHA, BETA, DELTA, OR OMICRON VARIANTS AND SUB VARIANTS

CROSS-REFERENCE TO RELATED APPLICATIONS

This application claims the benefit of the filing dates of earlier filed U.S. Provisional Application Nos. 63/391,414 and 63/413,045, filed 22 Jul. 2022 and 4 Oct. 2022, respectively. The content of each of which applications is incorporated by reference herein in its entirety.

TECHNICAL FIELD

The present disclosure relates to the field of compositions for and methods of treating coronavirus infection, known as COVID-19, as well as other ailments referred to at times as post-COVID or long COVID in human subjects. In particular, combination drug products are disclosed comprising two or more active ingredients. These combination drug products, when administered to human subjects in need, have a potential to shorten a period during which patient experiences COVID symptoms, inhibit a development of severe symptoms of COVID-19, lessen a frequency for hospitalization, enhance a speedy recovery, and even have a potential for alleviating post-COVID symptoms, as well as those of long COVID.

Common symptoms of COVID-19 include fever, cough, fatigue, breathing difficulties, and loss of smell and taste. Complications from COVID-19 may include pneumonia and acute respiratory distress syndrome. An incubation period is typically around five days but may range from one to 14 days.

People who experience post-COVID or long COVID conditions most commonly report tiredness or fatigue that interferes with daily life. Some report symptoms that get worse after physical or mental effort (also known as "post-exertional malaise"). Still others suffer from a fever, respiratory and heart symptoms, difficulty breathing or shortness of breath, cough, chest pain, fast-beating or pounding heart (also known as heart palpitations).

Neurological symptoms include difficulty thinking or concentrating (sometimes referred to as "brain fog"), headache, sleep problems, dizziness when standing up (lightheadedness), pins-and-needles feeling, loss of or change in smell or taste, and depression or anxiety.

Still others complain of digestive symptoms, such as diarrhea and stomach pain. Other symptoms reported include joint or muscle pain, rash, or even changes in menstrual cycles.

Despite the development of several vaccines, and emerging treatment protocols, transmission and infection remains high, as the virus mutates into different forms, including sub variants thereof. A resistance of or unwillingness in certain segments of the population to get vaccinated exacerbates the continuing spread of new infections and re-infections. Highly infectious sub variants of the omicron (B.1.1.529) variant of SARS-CoV-2, such as BA.2.12.1, BA.4 and BA.5, are currently outcompeting prior BA.1 and BA.2 sub variants and causing breakthrough infections even in fully vaccinated and boosted members of the population. Hence, there remains a continuing need in the art for new and effective treatments for patients suspected of harboring a coronavirus (even if asymptomatic) or exhibiting symptoms of an infection.

SUMMARY OF THE INVENTION

The present invention provides important combination drug products useful for inhibiting replication of SARS-CoV-2 virus, its variants and sub variants thereof, as well as in the treatment of active or acute COVID-19 disease and the prevention of long COVID and in all its forms. Generally, the combination drug products include at least two active ingredients, disulfiram and mercaptopurine, a prodrug thereof (azathioprine), or a hydrate thereof in an amount effective to inhibit viral replication. In certain embodiments, a third active ingredient, dexamethasone or a pharmacologically acceptable salt thereof (e.g., acetate anhydrous, lactose monohydrate, disodium phosphate) in an amount effective to alleviate inflammation is also included. Various doses and dosage regimens of the combination drug products are described for use after exposure to a coronavirus, for treatment of the acutely infected, or for maintenance doses for those exhibiting chronic effects from post-COVID or long COVID conditions.

The present disclosure provides compositions and methods having an end goal of eliminating circulating virion particles by inhibiting viral replication, among other possible mechanisms. It is important to note that while a preferred and convenient embodiment of a combination drug product is a single dosage form of either a two- or a three-component combination, the technology described can work equally effectively by administration of each component sequentially or contemporaneously (at the same time). Hence, the claims directed to the present subject matter should be so construed as to encompass single or multiple dosage forms comprising one or more of the desired components.

DETAILED DESCRIPTION OF PREFERRED EMBODIMENTS

In a preferred embodiment a combination drug product is disclosed comprising disulfiram and mercaptopurine, or a prodrug thereof (azathioprine), or a hydrate thereof in a two-drug combination product. In another preferred embodiment a combination drug product is disclosed comprising disulfiram, mercaptopurine, a prodrug of mercaptopurine (namely, azathioprine), or a hydrate of mercaptopurine and dexamethasone or a pharmacologically acceptable salt thereof in a three-drug combination product. Each of the foregoing compounds is known in the art, but not in the combination drug products described herein. Importantly, the combination drug products described herein do not include (indeed, excludes) the use, presence, or addition of any amounts of ivermectin, hydroxychloroquine and/or doxycycline.

Disulfiram is an alcohol antagonist drug. Its chemical name is bis(diethylthiocarbamoyl) disulfide and structural formula is:

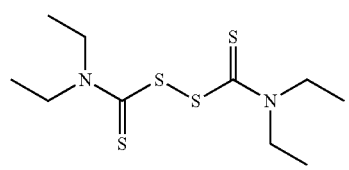

$C_{10}H_{20}N_2S_4$ M.W. 296.54

Disulfiram occurs as a white to off-white, odorless, and almost tasteless powder, soluble in water to the extent of about 20 mg in 100 mL, and in alcohol to the extent of about 3.8 g in 100 mL. Each tablet for oral administration contains 250 mg or 500 mg disulfarim, USP. Tablets also contain collodial silicon dioxide, anhydrous lactose, magnesium sterate, microcrystalline cellulose, sodium starch glycolate, and stearic acid.

Mercaptopurine is a nucleoside metabolic inhibitor. The chemical name is 6H-purine-6-thione, 1,7-dihydro-, monohydrate. The molecular formula is $C_5H_4N_4S \cdot H_2O$ and the molecular weight is 170.20. Its structural formula is:

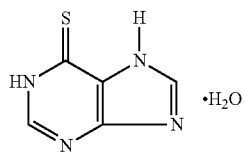

Mercaptopurine is a yellow, crystalline powder. Mercaptopurine is practically insoluble in water and in ether. It has a pKa of 7.8, an average tapped density of 1.0 g/ML and average bulk density of 0.85 g/mL. It dissolves in solutions of alkali hydroxides. PURINETHOL is available for oral use. Each scored tablet contains 50 mg mercaptopurine and the following inactive ingredients: corn starch, pregelatinized, potato starch, lactose, magnesium sterate and stearic acid.

Azathoprine, an immunosuppressive antimetabolite, is available in tablet form for oral administration. Each scored tablet contains 50 mg, 75 mg or 100 mg azathoprine, USP and the inactive ingredients anhydrous lactose, magnesium stearate, povidone, pregelatinized starch (corn starch), and stearic acid. Azathoprine is chemically 1H-Purine, 6-[(1-methyl-4-nitro-1H-imidazol -5-yl)thio]-. The structural formula of azathoprine is:

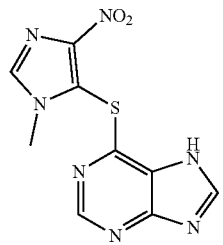 [SMILES: Cn1cnc([N+](=O)[O-])c1Sc1ncnc2nc[nH]c12]

It is an imidazolyl derivative of 6-mercaptopurine and many of its biological effects are similar to those of the parent compound. Azathoprine, USP is insoluble in water, but may be dissolved with addition of one molar equivalent of alkali. Azathoprine, USP is stable in solution at neutral or acid pH but hydrolysis to mercaptopurine occurs in excess sodium hydroxide (0.1N), especially on warming. Conversion to mercaptopurine also occurs in the presence of sulfhydryl compounds such as cysteine, glutathione and hydrogen sulfide.

Dexamethasone Tablets USP, 1.5 mg contain lactose monohydrate, magnesium sterate, starch and compressible sugar. Dexamethasone, a synthetic adrenocortical steroid, is a white to practically white, odorless, crystalline powder. It is stable in air. It is practically insoluble in water. The molecular formula is $C_{22}H_{29}FO_5$. The molecular weight is 392.47. Is is designated chemically as 9-fluoro-11β,17,21-trihydroxy-16α-methylpregna-1,4-diene-3,20-dione and its structural formula is:

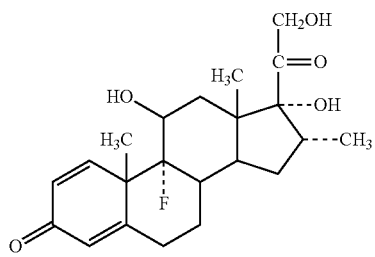

Accordingly, a method of inhibiting viral replication in a human subject suspected of suffering from or testing positive for a coronavirus infection is described comprising administering to the human subject in need thereof a combination drug product comprising disulfiram and mercaptopurine, a prodrug thereof, or a hydrate thereof in an amount effective to inhibit viral replication. A useful prodrug of mercaptopurine is azathioprine. Also described is a method using a three-component combination drug product comprising dexamethasone or a pharmacologically acceptable ester or salt thereof. Dexamethasone can be anhydrous, provided as an acetate or other ester, mixed with lactose monohydrate, or presented as a salt, such as disodium phosphate), in an amount effective to alleviate inflammation.

The disclosed combination drug product may be administered to a human subject by a variety of means or modalities, including, but not limited to, oral, gingival, lingual or sublingual, dermal or transdermal patch, lotion, or cream, ointment, rectal, nasal, ophthalmic, parenteral administration, or combinations thereof. Suitable amounts of each component drug to be administered at least once, preferably twice daily, include, but are not limited to, a dosage ranging from about 1 mg to about 4000 mg of disulfiram per day and from about 0.5 mg to about 3000 mg of mercaptopurine per day or from about 0.5 mg to about 3000 mg of azathiopurine per day. A dosage for a third component, dexamethasone, ranges from about 2 mg to about 32 mg of dexamethasone per day. Thus, a preferred method (and combination drug product) contemplated by the disclosure includes the use of a dosage form comprising disulfiram (present in amounts ranging from about 1 mg to about 4000 mg), mercaptopurine (present in amounts ranging from about 0.5 mg to about 3000 mg) or azathiopurine (present in amounts ranging from about 0.5 mg to about 3000 mg) and dexamethasone (present in amounts ranging from about 2 mg to about 32 mg). It is understood that the preferred daily dosages described may be achieved by an administration of one or more smaller or lower doses, which add up to the preferred daily dosages. By the same token, the preferred daily dosages may be reduced or exceeded, as specific circumstances might dictate or at the discretion of a prescribing physician or medical practitioner.

Additional suitable dose ranges include, but are not limited to, the following: For disulfiram, doses can range from about 22 mg to about 911 mg per day, from about 133 to about 388 mg per day, and from about 97 mg to about 137 mg per day; for mercaptopurine, doses can range from about 87 mg to about 222 mg per day, from about 109 mg to about 203 mg per day, from about 121 mg to about 161 mg per day; for azathiopurine, doses can range from about 0.1 mg to about 482 mg per day, from about 13 mg to about 469 mg per day, from about 91 mg to about 241 mg per day, from about 129 mg to about 213 mg per day; for dexamethasone, doses can range from about 2 mg to about 32 mg per day, from about 3 mg to about 23 mg per day, from about 6 mg to about 11 mg per day, from about 7 mg to about 9 mg per day. A dosage form comprising 250 mg of disulfiram and 25 mg of 6-mercaptopurine is contemplated, in one embodiment. Dosage forms can be administered once, twice, thrice, or more daily.

The methods and compositions described are useful for treating human subjects suffering from one or more symptoms of COVID-19, post-COVID, or long COVID. Besides a utility for treating an acute infection, the disclosed methods and compositions can also be used for a prophylactic or maintenance regimen to either prevent or alleviate post-COVID or long COVID symptoms. The utility of the technology for prophylaxis or maintenance is preferably achieved using amounts of each of the active ingredients, which are lower than those described for treating an acute or active infection.

A two-drug "low" dose combination product for treating post-COVID or long COVID symptoms preferably comprises disulfiram (122 mg) and mercaptopurine (109 mg) taken once a day over a duration of 7, 10, 14, or 28 days, as needed.

It is understood that human subjects who are candidates for the disclosed methods and compositions are those who have tested positive for an antigen or nucleic acid consistent with an infection caused by SARS-CoV-2, its alpha, beta, delta, or omicron variants or sub variants thereof.

Accordingly, a method is described for treating a human subject suspected of suffering from or testing positive for a coronavirus infection comprising administering to the human subject in need thereof a combination drug product comprising disulfiram and mercaptopurine, a prodrug thereof (such as azathioprine), or a hydrate thereof in an amount effective to alleviate one or more negative effects of said infection. In some embodiments of this technology the combination drug product further comprises dexamethasone or a pharmacologically acceptable ester or salt in an amount effective to alleviate inflammation.

Periods of treatment for an acute infection may vary, but, generally, may last until the human subject being treated tests negative for an infection from a coronavirus, such as SARS-CoV-2, its alpha, beta, delta, or omicron variants or sub variants thereof. Typical treatment periods may include, but are not limited to, a period of about 4 days to about 14 days, a period of about 5 days to about 12 days, and a period of about 7 days to about 9 days. Suitable other treatment periods may include, but are not limited to, a period of about 5 days to about 28 days, a period of about 7 days to about 14 days, and a period of about 9 days to about 12 days. In other embodiments of the present method, treatment duration can last up to about 5, about 7, about 10, or about 14 days.

While a person of ordinary skill in the art might envision a number of combination drug products from the descriptions provided, the disclosure specifically contemplates a combination drug product comprising disulfiram and mercaptopurine, a prodrug thereof (namely, azathioprine), or a hydrate (e.g., a monohydrate) thereof. Also specifically contemplated is a combination drug product comprising disulfiram, mercaptopurine (or azathioprine), and dexamethasone or a pharmacologically or pharmaceutically acceptable salt thereof. The contemplated combination drug products may further comprise one or more pharmaceutically acceptable carriers. Moreover, the combination drug products can take any suitable dosage form, including any solid, dermal, gel, or liquid dosage form.

Methods described herein include those for inhibiting replication of coronavirus, its variants and sub variants and prevention or amelioration of COVID-19 and conditions related to post-COVID and/or long COVID. In one aspect, the methods include an administration of one or more combination drug products to human subjects who are suspected of harboring a coronavirus (e.g., persons that were exposed to another who has since tested positive for a coronavirus infection), who have tested positive for a coronavirus infection, or who are recovering from a coronavirus infection. Human subjects may be at risk of viral infection or exposure to coronavirus, may be individuals identified as having been infected with coronavirus, or may be of an age (very young children or elderly) or may have an underlying condition placing them at a high risk of severe adverse consequences from an infection.

However, individuals may be symptomatic or asymptomatic. Thus, "therapeutic" use of the combination drug product refers to processes that are intended to produce a beneficial change in an existing condition (e.g., viral infection) of the subjects, such as by reducing the severity of the clinical symptoms and/or effects of the infection, and/or reducing the duration of the infection/symptoms/effects. Likewise, "prophylactic" use of the combination drug product refers to processes that are intended to inhibit or ameliorate the effects of a future viral infection to which subjects may be exposed (but is not currently infected with). In some cases, the combination drug products may prevent the development of observable morbidity from viral infection (i.e., near 100% prevention). In other cases, the combination drug products may only partially prevent and/or lessen the extent of morbidity due to the viral infection (i.e., reduce the severity of the symptoms and/or effects of the infection, and/or reduce the duration of the infection/symptoms/effects). In either case, the combination drug products are still considered to "prevent" the target infection.

Additional ingredients may be included in the production of complete combination drug products, including other active agents, preservatives, buffering agents, salts, carriers, excipients, diluents, or other ingredients.

All of the foregoing percentages are based on the total weight of the combination drug products taken as 100% by weight, including the two- or three-component combination drug products and those containing additional other ingredients.

The term "salt," "hydrate," or "solvate" refers to an interaction between a defined compound and one or more molecules of an acid or base (organic or inorganic acids or bases, more below), water, or solvent to form a stabilized salt, hydrate, or solvate species; "metabolites" refers to a defined compound that has been metabolized in vivo by digestion or other bodily chemical processes; and "prodrugs" refers to a defined compound that has been generated by a metabolic process. As such, azathioprine is a prodrug of mercaptopurine, and mercaptopurine is a metabolite of azathioprine. The compounds can be directly used in partial or essentially completely purified forms, or can be modified as indicated above. The compounds may be in amorphous, crystalline, or lyophilized forms.

Some or all of the ingredients can be in the form of acceptable esters or salts. The esters and salts should be generally safe, non-toxic, and neither biologically nor otherwise undesirable and are acceptable for human use, and which possess the desired degree of activity. Accordingly, the recitation herein of the active ingredients is intended to embrace not only the named ingredients, but also any acceptable esters or salts thereof.

"Pharmaceutically acceptable salts" with reference to the components means salts of the components which are pharmaceutically acceptable, i.e., salts which are useful in preparing pharmaceutical compositions that are generally safe, non-toxic, and neither biologically nor otherwise undesirable and are acceptable for human pharmaceutical use, and which possess the desired degree of pharmacological activity. Such pharmaceutically acceptable salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in Handbook of Pharmaceutical Salts Properties, and Use, P. H. Stahl & C. G. Wermuth eds., ISBN 978-3-90639-058-1 (2008).

In one or more embodiments, in solid dosage form, blended powders should optionally be of a size to pass through a 50-mesh screen while being retained by a 100-mesh screen. Still further, the blended powders are placed in capsules for ease of dosage. The capsules or tablets can each contain from about 25-5000 mg of the blended powders, preferably from about 100 mg to about 1500 mg, most preferably less than about 1000 mg of the blended powders. While such powdered combination drug products are preferred for ease of manufacture and administration, it should be understood that the invention is not so limited. For example, the blended ingredients may be prepared as liquid dispersions or solutions using appropriate, non-interfering dispersants or solvents; other possible dosage forms include gels, suspensions, or solids such as tablets or pills.

Use of Combination Drug Products

In use, therapeutically effective amounts of the combination drug product are administered to a mammalian subject in need thereof for a therapeutically effective amount of time. As used herein, an "effective" amount refers to the dosage amount and/or duration that will elicit the biological or medical response of a tissue, system, or subject that is being sought by a researcher or clinician, and in particular elicit some desired therapeutic effect as against the coronavirus cells by slowing and/or inhibiting activity, growth, or replication of the cells. One of skill in the art recognizes that an amount or duration may be considered "effective" even if the condition is not totally eradicated or prevented, but it or its symptoms and/or effects are improved or alleviated partially or inhibited from worsening in the subject. Such effective dosages and durations may comprise a single unit dosage or, more usually, periodic (e.g., daily or weekly) administration of lower dosages over time.

Moreover, in the context of the disclosure a combination drug product is administered to human subjects in an amount effective to inhibit viral replication, such as, for example, the presence of a virus in a sample taken from a patient can no longer be detected by a test, such as viral antigen test or a viral nucleic acid amplified oligonucleotide probe-based test, designed to detect trace amounts of virion particle or fragments thereof. By the same token, such amounts of combination drug product are administered in an amount effective to alleviate one or more negative effects of acute viral infection so that the infected individual recovers from the individual's symptoms. For human subjects, especially those who have suffered a second, third, or more bouts of coronavirus infection, following a prophylactic or maintenance dose regimen would provide amounts of combination drug product, which are effective to inhibit or prevent reinfection and/or suppress symptoms or negative effects of post-COVID or long COVID. Similarly, the administration of the described amounts of dexamethasone are designed to be effective in significantly reducing or eliminating inflammation in an afflicted human subject to allow the individual to make a steady and substantial recovery. Additional details of viral replication inhibition are provided, below.

The combination drug products of the invention, in whatever physical form, are designed for administration to humans, in particular those exposed, or potentially exposed, to the SARS-CoV-2 virus, its variants and sub variants thereof, or those suffering from the COVID-19 disease. The combination drug products may be administered in any convenient manner, such as by oral, rectal, nasal, ophthalmic, parenteral (including intraperitoneal, gastrointestinal, intrathecal, intravenous, cutaneous (e.g., dermal patch), subcutaneous (e.g., injection or implant), or intramuscular) routes. In one or more embodiments, the dosage forms are administered in repeated dosages, e.g., daily, multiple time daily, and the like. Where the aforementioned capsules are used, the administration would be oral, and the recommended dosage level would be, in one embodiment, one to four such capsules per day, taken twice daily. Dosage forms may be administered with a meal, or suspended or dissolved in a fat-containing liquid before administration, or co-administered with such fatty substances. A clinician or researcher may determine the appropriate administration protocol depending upon the dosage form and route of administration used.

The combination drug product may be administered in conjunction with other recommended therapies for treating COVID-19 or its symptoms. The combination drug product may also be taken prophylactically, such as during period of time where there is high community transmission of SARS-CoV-2, its variants and sub variants thereof. The methods can be also applied for clinical research and/or study.

Additional advantages of the various embodiments of the invention will be apparent to those skilled in the art upon review of the disclosure herein. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

Levels of dosing to human subjects of the combination drug products hereof are quite variable owing to factors such as the patient's age, patient's physical condition and the severity of the disease. In general, however, regardless of the dosage form or route of administration employed, the combination drug products should be dosed from about 1 mg to about 4000 mg per day of disulfiram, from about 0.5 mg to about 3000 mg per day of mercaptopurine, from about 0.5 mg to about 3000 mg per day of azathioprine, if used in place of mercaptopurine, and from about 2 mg to about 32 mg per day of dexamethasone. Such dosages may be based on a single administration per day, but more usually multiple administrations per day. One suitable dosage regimen, includes administration of 375 mg of disulfiram and 75 mg of mercaptopurine as a morning dose, while 250 mg of disulfiram and 50 mg of mercaptopurine is administered as an evening dose. Yet another suitable dosage regimen involves administration of 250 mg disulfiram BID and 25 mg mercaptopurine BID. The timing of administration over a 24 hour period can be adjusted as needed, including administration with food or without food.

As used herein, the term "inhibit" refers to a reduction or decrease viral titer or quantity, compared to a baseline. For example, in the context of the present invention, inhibition of viral replication refers to a decrease in amount or speed of viral replication as compared to baseline (e.g., as detected by a rapid antigen test, or molecular/PCR test, or other suitable testing methodology). By comparing a baseline obtained before administration of the combination drug product to the values obtained from the individual after administration of the combination drug product, those of ordinary skill in the art can readily determine whether or not viral replication has been inhibited and to what extent. Thus, an "amount effective" to inhibit viral replication refers to the amount of a given combination drug product that results in a reduced level of viral replication and thus a reduced amount of detectable virus in the individual (e.g., reduced viral titer or viral load) when comparing the baseline detected amount to the reduced amount using the same testing methodology. Preferably, prophylactic and/or therapeutic methods of the invention will lead to a decrease of at least 20%, at least 30%, at least 40%, at least 50%, at least 60%, at least 70%, at least 80%, or even at least 90% as compared to the baseline. Preferably, such reductions are seen within 72 hours after administration, preferably within 48 hours, preferably within 36 hours, more preferably within 24 hours. Correspondingly, such reductions in viral load will advantageously lead to an amelioration, improvement, or decrease in one or more symptoms associated with coronavirus infection and/or reduced transmission of the virus from the infected individual to others. Alternatively, inhibition or antiviral efficacy can be assessed in vitro. In one or more embodiments, the combination drug product will inhibit viral replication by at least 50% in a cell-based assay, preferably by at least 60%, 70%, 80%, or 90% in a cell-based assay. Preferably, the combination drug product will have a Selectivity Index of greater than 1, preferable of at least 3, more preferably at least 5, and more preferably at least 6. The Selectivity Index is the ratio of the toxic concentration of a combination drug product against its effective bioactive amount. In one or more embodiments, the toxic concentration is the dose that leads to 50% cell cytotoxicity in an in vitro cell assay. In one or more embodiments, the bioactive amount is the dose that inhibits viral replication by 90% in a cell assay.

It is important to note, however, that efficacy can also be measured by a decrease or outright elimination (in frequency and/or intensity) of coronavirus symptoms compared with COVID-19 symptoms before intake of the proposed combination drug product. Efficacy can also be characterized by a lack of a "rebound" effect in which recovered COVID patients treated with PAXLOVID™ become positive for coronavirus antigen a few days to several days after testing negative for coronavirus antigen. The Centers for Disease Control also cautions that coronavirus antigen can linger in a recovered, asymptomatic patient's system weeks or even months after recovery.

EXAMPLES

The following example sets forth methods in accordance with the technology disclosed. It is to be understood, however, that this example is provided by way of illustration and nothing therein should be taken as a limitation upon the overall scope of applications of the technology.

Materials and Methods

Disulfiram, mercaptopurine, azathioprine and dexamethasone are all known compounds individually. Methods for their preparation can be found in the literature. For example, disulfiram (tetraethylthiuram disulfide) is available from Sigma-Aldrich, Product No. 86720. Also, 6-mercaptopurine monohydrate is available from Sigma-Aldrich, Product No. 852678. Likewise, azathioprine can be obtained from the same vendor, Product No. A4638, and the same for dexamethasone, Product No. D4902.

For tablet dosage forms 312 mg of disulfiram is mixed with 72 mg of mercaptopurine and pharmaceutically acceptable carriers, such as cornstarch, colloidal silicon dioxide, anhydrous lactose, magnesium stearate, microcrystalline cellulose, sodium starch glycolate and stearic acid. Azathioprine (72 mg) can be used in place of the mercaptopurine. For a three-component combination drug product, 10 mg of dexamethasone can be added to the aforementioned mixture. Preferably, each tablet is taken orally twice a day for patients with an acute or active infection. The mixtures can also be formulated into gelatin capsules. Other dosage forms can be manufactured, thus, whether in solid or liquid forms. Other inactive ingredients include, but are not limited to, lactose monohydrate, compressible sugar, pre-gelatinized potato starch and povidone. Preferably, the aforementioned dosage forms are taken twice daily if the human subject is suffering from an acute coronavirus infection. The acutely infected patient may take this medication for a period of time lasting from about 5 days to about 14 days, preferably, from about 7 days to about 10 days.

For tablet dosage forms to 122 mg of disulfiram is mixed with 109 mg of mercaptopurine and pharmaceutically acceptable carriers, such as cornstarch, colloidal silicon dioxide, anhydrous lactose, magnesium stearate, microcrystalline cellulose, sodium starch glycolate and stearic acid. Azathioprine (109 mg) can be used in place of the mercaptopurine. Preferably, each tablet is taken orally once a day for patients with post-COVID or long COVID symptoms. The chronically symptomatic patient may take this medication for a period of time lasting from about 7 days to about 14 days, preferably, from up to about 28 or more days, or until the patient's symptoms fade.

In Vitro Assay of COVID 19 Using Combination Drug Product

The antiviral activity of a combination drug product on coronavirus is assessed in vitro using novel coronavirus SARS-CoV-2 isolate USA-WA1/2020 (deposited by the Centers for Disease Control and Prevention). For propagation and experimentation with SARS-CoV-2, Vero E6 (ATCC.®. CRL-1586.™.) cells are maintained in EMEM (Eagle's Minimum Essential Medium) cell culture media (cat #30-2003, ATCC, Manassas, Va., USA) supplemented with 2% or 10% fetal bovine serum (FBS), 100 U/mL penicillin, 100 μg/mL streptomycin, 0.01M HEPES buffer solution, 1 mM sodium pyruvate, 1× non-essential amino acids solution (cat #SH3023801, Thermo Fisher Scientific, Waltham, Mass., USA) and 2 mM L-glutamine.

The combination drug product in a form of a powder containing a mixture of disulfiram and mercaptopurine is tested. The powder blend is suspended in aqueous ethanol in a 1:10 wt:volume ratio, centrifuged and filter sterilized. A similar filter sterilized suspension is prepared, this time including a third component of dexamethasone. The suspensions are set aside.

Plated cells are first infected with SARS-CoV2 at a multiplicity of infection (MOI) of 0.001. The combination drug products (in separate tests) are then added during and post-infection. At 72 hours post-infection, the cell monolayers are stained with crystal violet to determine the level of cytopathic effect (CPE). The CPE level is quantified to determine the $IC_{90}$ (dose that inhibited viral replication by 90%). Vero cells are also treated with the test combination drug products alone for 24 hours to determine the $CC_{50}$ (dose that leads to 50% cell cytotoxicity). After 24 hours of treatment, cell viability is determined by a standard MTS colorimetric assay. Based on the $IC_{90}$ and $CC_{50}$, the Selectivity Index ($CC_{50}/IC_{90}$) of each of the treatments is determined to show safe and effective antiviral activity against SARS-CoV-2 infection. Similar outcomes are expected for the variants of SARS-CoV-2, including sub variants of the omicron variant.

Treatment of Human Subjects

A 64-year-old female previously vaccinated tests positive for a coronavirus infection using a swab test. Her symptoms are classic: sore throat, coughing, shortness of breath, oxygen tension of 92% and some diarrhea but no loss of smell or taste. She is treated with a two-drug combination product, (312 mg of disulfiram and 72 mg of mercaptopurine, as described above, twice daily). She tests negative after the $7^{th}$ day of treatment.

A 45-year-old male presents with symptoms of coronavirus infection with tiredness, rigors, fever, and loss of taste and smell. A nasal swab sample is taken from the patient and following a test (coronavirus PCR kit) confirms positive for a coronavirus infection. He is treated with a three-drug combination product, (312 mg of disulfiram, 72 mg of mercaptopurine and 10 mg of dexamethasone, as described above, twice daily). He tests negative after the $5^{th}$ day of treatment.

A 35-year-old female presents with symptoms of long COVID after being acutely infective with an omicron variant and following a three-week recovery in a hospital. She complains of being chronically tired, experiences occasional brain fog and has an altered menstrual cycle. She is treated with a low dose two-drug combination product, (122 mg of disulfiram and 109 mg of mercaptopurine, as described above, once daily). Her symptoms fade after the $28^{th}$ day of treatment.

A 65-year-old male presents on Day 0 with symptoms of a scratchy throat, chills and some body aches. Body temperature rises to 100.8° F. On Day 1, coughing, sore throat and elevated temperature is observed (101° F.). Retains ability to smell percolating coffee. Tests positive using an antigen test (faint line, but positive). Patient feels very tired; tries to get sleep but urge to cough is strong overnight preventing ability to stay asleep. Throat is extremely sore from coughing. On Day 2, takes 375 gm of disulfiram and 75 mg of mercaptopurine at 14:30. Takes another dose of disulfiram (250 mg) and mercaptopurine (50 mg) at 21:30. Goes back to bed in an attempt to get more sleep. Gets up at 01:30 to go to the bathroom; feels different, feels better, symptoms appear to have been arrested suddenly. On Day 3, takes 375 gm of disulfiram and 75 mg of mercaptopurine at 08:30. Coughing very infrequently now; throat feels like it is on the mend. No longer feeling a strong urge to cough. Body temperature 97.9° F. So far, not detecting any adverse effects. At 15:45, tested positive using an antigen test. Takes another dose of disulfiram (250 mg) and mercaptopurine (50 mg) at 21:00. On Day 4, records temperature of 97.3° F., takes 375 gm of disulfiram and 75 mg of mercaptopurine at 09:15. Continues to feel good. Tests positive using an antigen test, 17:45; records a temperature of 97.3° F. Experiences an occasional cough over the course of the day. Takes another dose of disulfiram (250 mg) and mercaptopurine (50 mg) at 22:00. Continues twice daily dosage regimen for Days 5 & 6, with little to no symptoms and no apparent adverse effects. (Positive antigen tests on Days 5 & 7 dismissed as false positives, likely from continued shedding of virion proteins from residual, disabled virus.) On Day 9, obtains a PCR (viral RNA) test from Quest Diagnostics (11:00). Quest Diagnostics reports detection of viral RNA on Day 10 from the patient sample; again, dismissed as false positive. Very surprisingly and unexpectedly, patient's domestic partner never tests positive despite repeated antigen testing during first week of patient's acute infection, with no precautions (no masks, no distancing, sleeping in the same bed). The treatment regimen appears to have inhibited spread of the viral infection to patient's domestic partner. Patient tested negative using an antigen test on Day 41.

A 72-year-old female weighing approximately 155 lbs. contracts COVID-19 and exhibits the usual coronavirus symptoms, including an elevated temperature. She takes 375 mg disulfiram and 75 mg of mercaptopurine at the outset, followed by 250 mg disulfiram and 50 mg of mercaptopurine as a second dose of a twice-daily regimen. She feels better within one day of taking her first dose, but she experiences diarrhea as well. She is asymptomatic for COVID-19 after completing a second straight day of morning and evening dosing at the aforementioned dosage levels. Her diarrhea continues at a level that she cannot tolerate, and she agrees to halt taking the two-drug combination regimen. Her diarrhea improves, while her COVID-19 symptoms never return over the next few days. While not being held to theory, her diarrhea might be attributable to the intake of mercaptopurine—for which 9% of leukemia patients experienced diarrhea. Diarrhea is not mentioned in a list of adverse reactions for disulfiram.

A 57-year-old female weighing approximately 155 lbs. develops bronchitis, but is otherwise healthy. She tests negative for COVID-19 using a rapid antigen test. She takes 250 mg disulfiram and 50 mg of mercaptopurine at the outset, followed by 250 mg disulfiram and 50 mg of mercaptopurine as a second dose of a twice-daily regimen. She undergoes two more days of twice-daily oral administration of 250 mg disulfiram and 50 mg of mercaptopurine without effect (i.e., still coughing from her bronchitis). She does not exhibit any apparent adverse effects from the three days of treatment.

An alternative and preferred dosage regimen could be 250 mg disulfiram BID and 25 mg mercaptopurine BID. One of ordinary skill in the art would have the wherewithal to arrive at a suitable dosing regimen for both drugs, which would maximize the therapeutic index while minimizing adverse side effects, without undue experimentation.

Yet another alternative and preferred dosage regimen could involve use of a new dosage form (e.g., a capsule, tablet, or the like) containing 384 mg disulfiram and 112 mg mercaptopurine, which can be taken orally once-a-day. Other once-a-day dosage forms can be contemplated containing varying amounts of disulfiram and mercaptopurine, which would facilitate convenience on the part of a COVID-19 or long COVID patient. Other coronaviruses, which utilize the same or similar four essential non-structural proteins as SARS-CoV-2 for replication, like the coronavirus that causes Middle East Respiratory Syndrome (MERS), should also be susceptible to the drug combinations described herein. These four essential non-structural proteins include papain-like protease, helicase, RNA-dependent RNA polymerase and 3-chymotrypsin-like protease.

A number of embodiments of the invention have been described. Nevertheless, it can be understood that various modifications may be made without departing from the spirit and scope of the invention. Accordingly, other embodiments are within the scope of the following claims.

What is claimed is:

1. A method of inhibiting viral replication in a human subject testing positive for a coronavirus infection, the method comprising administering to the human subject an oral daily dose of a combination drug product, wherein the oral daily dose comprises (i) a first dose of at least 375 mg of disulfiram and at least 75 mg of mercaptopurine or azathioprine, and (ii) a second dose of at least 250 mg of disulfiram and at least 50 mg of mercaptopurine or azathioprine.

2. The method of claim 1, in which the combination drug product further comprises from about 2 mg to about 32 mg of dexamethasone or a pharmacologically acceptable ester or salt thereof.

3. The method of claim 1, in which the oral daily dose is administered to the human subject in solid, gel, or liquid dosage form.

4. The method of claim 1, in which the human subject exhibits one or more symptoms of COVID-19 or long COVID prior to the administration.

5. The method of claim 1, in which the human subject tested positive for an antigen or nucleic acid consistent with an infection caused by SARS-COV-2, its alpha, beta, delta, or omicron variants or sub variants thereof.

6. An oral combination drug product, in dosage form, comprising (i) a first dose of at least 375 mg of disulfiram and at least 75 mg of mercaptopurine or azathioprine, and (ii) a second dose of at least 250 mg of disulfiram and at least 50 mg of mercaptopurine or azathioprine.

7. The oral combination drug product of claim 6, further comprising from about 2 mg to about 32 mg of dexamethasone or a pharmacologically acceptable salt thereof.

8. The oral combination drug product of claim 6, further comprising one or more pharmaceutically acceptable carriers.

9. The oral combination drug product of claim 8 in solid, gel, or liquid dosage form.

* * * * *

(12) SUPPLEMENTAL EXAMINATION CERTIFICATE

United States Patent  
Naeger

(10) Number: US 11,986,479 F1  
(45) Certificate Issued: Jan. 22, 2025

Control No.: 96/050,065

Filing Date: Nov. 1, 2024

Primary Examiner: Shri Ponnaluri

No substantial new question of patentability is raised in the request for supplemental examination. See the Reasons for Substantial New Question of Patentability Determination in the file of this proceeding.

(56) Items of Information

OTHER DOCUMENTS

1. Discussion of 35 U.S.C.§ 112(a) for claims 2 and 7 on pages 2-5 of the request.